United States Patent [19]

Nomura et al.

[11] Patent Number: 5,315,040
[45] Date of Patent: May 24, 1994

[54] PRODUCTION OF AROMATIC AMINES

[75] Inventors: Kotohiro Nomura; Masaru Ishino, both of Ibaraki, Japan

[73] Assignee: Sumitomo Chemical Company, Limited, Osaka, Japan

[21] Appl. No.: 829,250

[22] Filed: Feb. 3, 1992

Related U.S. Application Data

[62] Division of Ser. No. 604,520, Oct. 29, 1990, Pat. No. 5,112,997.

[30] Foreign Application Priority Data

Oct. 31, 1989 [JP] Japan .................. 1-285571
May 31, 1990 [JP] Japan .................. 2-143377
Aug. 24, 1990 [JP] Japan .................. 2-222770

[51] Int. Cl.$^5$ ......................... C07C 209/36
[52] U.S. Cl. ................................. 564/422
[58] Field of Search ........................ 564/422

[56] References Cited

U.S. PATENT DOCUMENTS

| | | | |
|---|---|---|---|
| 3,270,057 | 8/1966 | Cooke et al. | 260/580 |
| 3,293,295 | 12/1966 | Swakon et al. | 260/563 |
| 3,578,713 | 5/1971 | Scott et al. | 260/580 |
| 3,637,820 | 1/1972 | Dodman et al. | 260/508 |
| 3,944,615 | 3/1976 | Iqbal | 260/58 |
| 3,975,411 | 8/1976 | Someshima et al. | 552/238 |
| 3,978,131 | 8/1976 | Pawellek et al. | 260/576 |
| 4,054,586 | 10/1977 | Hirai et al. | 552/238 |
| 4,256,670 | 3/1981 | Homeier | 564/416 |
| 4,540,817 | 9/1985 | Behre et al. | 564/218 |
| 5,087,755 | 2/1992 | Nomura | 564/422 |

FOREIGN PATENT DOCUMENTS

| | | |
|---|---|---|
| 0097592 | 4/1984 | European Pat. Off. . |
| 0293999 | 7/1988 | European Pat. Off. . |
| 2715072 | 10/1977 | Fed. Rep. of Germany . |
| 146287 | 2/1981 | Fed. Rep. of Germany . |

OTHER PUBLICATIONS

Ryan et al, (1979) *Journal of Molecular Catalysis*, pp. 319–330.
Abul F. M. Iqbal, (1971), *Tetrahedron Letters No. 37*, pp. 3385–3388.
M. Freifelder, (1971) John Wiley & Sons, Inc. eds., *Practical Catalytic Hydrogenation*, Wiley-Interscience, New York, pp. 168–169.
R. A. Sheldon, (1983) D. Reidel Publishing Co., *Chemicals From Synthesis Gas*, Dordrecht, Holland, pp. 178–181.
Okana et al. (1981) Chemistry Letters pp. 1083–1086.
Kaneda et al. (1981) Journal of Molecular Catalysis 12:385–387.
Ryan et al. (1979) Journal of Molecular Catalysis 5:319–330.
Alper et al. (1980) Tetrahedron Letters 21:2603–2604.
Alessio et al. (1982) Journal of Molecular Catalysis 19:113–116.
Cann et al. (1978) Journal American Chemical Society 100:3969–3971.
European Search Report.

*Primary Examiner*—Allen J. Robinson
*Assistant Examiner*—Brian M. Burn
*Attorney, Agent, or Firm*—Birch, Stewart, Kolasch & Birch

[57] ABSTRACT

Aminoanthraquinones which are materials for dyes are prepared by allowing nitroanthraquinones to react with carbon monoxide and water in a liquid phase in the presence of a homogeneous catalyst comprising rhodium compounds or ruthenium compounds and solvents therefor.

8 Claims, No Drawings

PRODUCTION OF AROMATIC AMINES

This application is a division of copending application Ser. No. 07/604,520, filed on Oct. 29, 1990, now U.S. Pat. No. 5,112,997. The entire contents of which are hereby incorporated by reference.

The present invention relates to production of aminoanthraquinones from nitroanthraquinones, particularly production of 1-aminoanthraquinone from 1-nitroanthraquinone. More particularly, the present invention relates to production of aminoanthraquinones by allowing nitroanthraquinones to react in a liquid phase, with carbon monoxide (hereinafter referred to as CO) and water in the presence of a homogeneous catalyst comprising ruthenium compounds or rhodium compounds and solvents.

The other aspect of the present invention relates to production of aromatic amines from aromatic nitro compounds excluding nitroanthraquinones (hereinafter referred to as aromatic nitro compounds) by use of CO and water.

Aminoanthraquinones including 1-aminoanthraquinone are useful as intermediates of anthraquinone dyes. The 1-aminoanthraquinone is prepared, for example, by sulfonating anthraquinone before amination, or nitrating anthraquinone before reduction.

Reduction of nitroanthraquinones which are the starting material of the present invention is carried out in various manners. One of the processes is reduction with metal powders such as iron in acid mediums such as sulfuric acid. Another process is reduction with, for example, alkali metal sulfide, alkali metal hydrogensulfide, hydrazin or glucose. Another process is allowing the nitroanthraquinones to react with ammonia until substitution with an amino group is effected. The other process is catalytic hydrogenation catalysts such as, palladium-carbon. None of the processes refer to production of aminoanthraquiones from nitroanthraquinones with CO and water.

Many difficulties are encountered in the conventional production of the aminoanthraquinones. One the processes where anthraquinone is sulfonated and then aminated has problems, i.e., small yield and reactivity in addition to trouble with catalysts, i.e., toxicity of mercury compounds and after-treatments of wasted water. Another process, where the nitroanthraquinone obtained by nitration of anthraquinone is reduced also has problems. Stoichiometric reduction with hydrogensulfides, for example, alkali metal hydrogensulfide creates problems, e.g., a treatment of inorganic salts by-produced and contamination of the product with the inorganic salts. Reduction with palladium-carbon causes various side-reactions such as reduction of carbonyl groups as well as the nitro groups, thereby decreasing yield of the desired aminoanthraquinone. Furthermore, separation of the catalysts from the reduction product needs so much labor that the reduction as a whole, is not economical.

Aromatic amines including aniline are useful as medicines, agricultural chemicals, dyes or pigments or intermediates thereof. The aromatic amines are produced by reducing aromatic nitro compounds in the presence of catalysts in a CO/water system. One of the processes, (1), is reduction of nitrobenzene in aqueous tetrahydrofuran/trimethylamine solution in the presence of rhodium or ruthenium catalysts (J. Am. Chem. Soc. 1978, 100, 3969). Another process, (2), is reduction of nitrobenzene or nitrotoluene in ethanol in the presence of chelate amines such as phenanthroline in addition to a rhodium or ruthenium catalyst (EP 0097592A; J. Mol. Catal., 18, 113, 1983; J. Mol. Catal., 22, 327, 1984).

Reduction of the aromatic nitro compounds with CO and water also has problems. In (1) above, a large amount of hydrogen is by-produced and large amounts of water and CO are exhausted due to the other side reactions than the desired reduction of the nitro group. A large amount of the trimethylamine, e.g., $10^3$ times as much as the metal in the catalyst is employed. The ruthenium catalysts to which trimethylamine is added, e.g., $Ru_3(CO)_{12}$-$NMe_3$ aq., are specifically active to water-gas-shift reaction where hydrogen and carbon dioxide are produced from the water and the CO (A.C.S. Symp. Ser., 152, 325, 1981).

In the case of (2) above, the nitro compounds to which the process is applied are restricted, since the literature mentions that the nitro compounds to which the process in issue are able to be applied should have such inert substituents as alkyl groups, alkoxy groups or amino groups. The catalysts where rhodium is a main metal reduce ketone groups as well as olefins, in the case of reduction of benzylideneacetone (J. Mol. Catal., 22, 327, 1984). In addition, catalytic activity is not so strong that high concentration of catalysts, high temperature, high pressure and a long period of time are necessary.

Under such situations, investigation was made on the reaction of aromatic nitro compounds with CO and water in a liquid phase in the presence of homogeneous catalysts. As a result, homogeneous catalysts comprising rhodium compounds or ruthenium compounds and solvents where found to facilitate catalytic activity and reduction of only nitro groups with selectivity as high as substantially 100% without damaging the anthraquinone skeleton, thereby obtaining aminoanthraquinones from nitroanthraquinones with reduction selectivity of the nitro groups of substantially 100%. The present invention is based on this finding.

According to one of aspects of the present invention, a process for preparing aminoanthraquinones is provided where nitroanthraquinones are allowed to react with CO and water in liquid phase in the presence of a homogeneous catalyst comprising rhodium compounds or ruthenium compounds and solvents.

The present invention also provides an improvement in the process for preparing aminoanthraquinones by allowing nitroanthraquinones to react with CO and water in the presence of a homogeneous catalyst comprising rhodium compounds or ruthenium compounds and solvents, reaction is effected in the presence of amine compounds together within the catalyst.

The present invention also provides a further improvement in the process for preparing aminoanthraquinones by allowing nitroanthraquinones to react, in a liquid phase, with CO and water in the presence of a homogeneous catalyst comprising ruthenium compounds and solvents, which is carried out by allowing copper compounds as well as the amine compounds to be present together with the catalyst.

In another aspect of the present invention, where aromatic nitro compounds are allowed to react with CO and water in the presence of a homogeneous catalyst comprising ruthenium compounds and solvents until aromatic amine compounds are obtained the, co-presence of specific amines facilitates selective reduction of the nitro groups without losing catalytic activity and by controlling by-reactions such as water-gas-shift reaction. For example, such a process would be where the aromatic nitro compounds are allowed to react with CO and water in the presence of a homogeneous catalyst comprising ruthenium compounds and solvents together with amine compounds of the formula $$H NR^4 R^5 \qquad (II)$$

wherein $R^4$ and $R^5$ are as defined below, to produce to aromatic amine compounds.

The present invention is explained in detail below.

The present process uses CO/water as a hydrogen source.

Starting compounds

The following is an example of the reaction for preparing aminoanthraquinones, nitroanthraquinone is used as when the starting nitroanthraquinone:

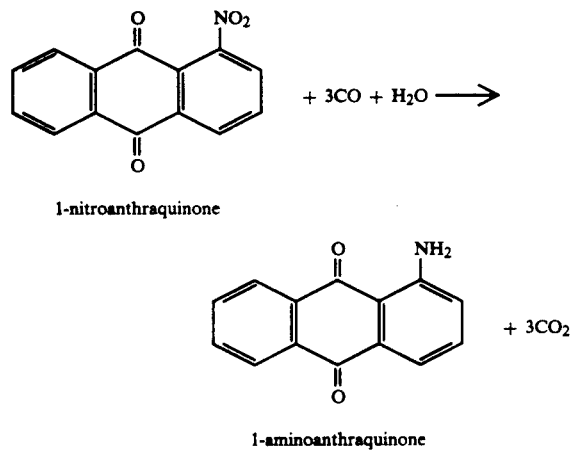

1-nitroanthraquinone 1-aminoanthraquinone 3 moles of CO is required for each 1 mol of nitro group with 3 moles of $CO_2$ being by-produced.

The present starting nitroanthraquinones are compounds having one or two nitro groups on an anthraquinone skeleton or those having such substituents as a sulfonate group, a halogen atom, a carboxyl group, or a hydroxyl group thereon. They are, for example, 1-nitroanthraquinone, 2-nitroanthraquinone, 1,2-, 1,3-, 1,4-, 1,5-, 1,6-, 1,7-, 1,8-, 2,3-, 2,6- or 2,7-dinitroanthraquinone, sodium 1-nitroanthraquinone-5-sulfonate, 1-nitroanthraquinone-5-carboxylic acid, 2-bromo-4-hydroxy-1-nitroanthraquinone, 2,4-dibromo-1-nitroanthraquinone, sodium 4-bromo-1-nitroanthraquinone-2-sulfonate or mixtures thereof. Preferred is a nitrated mixture containing mainly 1-nitroanthraquinone obtained by mono-nitrating anthraquinone and, as by-products, dinitroanthraquinone, etc., or pure 1-nitroanthraquinone obtained by purification of the above, from an economical viewpoint.

The aromatic nitro compounds, the starting material in the other aspect of the present process, are those having at least one nitro group on the aromatic ring, e.g., hydrocarbon ring such as benzene, naphthalene, anthracene, etc. or heterocyclic ring such as pyridine, quinoline, etc. The aromatic nitro compounds may have substituents such as an alkyl group, a halogen atom, an amino group, a hydroxyl group, a carboxyl group, an alkoxyl group, a cyano group or a sulfonic group. The aromatic nitro compounds usually employed are nitrobenzene, o-nitrotoluene, m-nitrotoluene, p-nitrotoluene, 2-nitro-p-xylene, o-chloronitrobenzene, m-chloronitrobenzene, p-chloronitrobenzene, p-cyanonitrobenzene, o-nitroaniline, m-nitroaniline, p-nitroaniline, o-dinitrobenzene, m-dinitrobenzene, p-dinitrobenzene, 2,4-dinitrotoluene, o-nitrophenol, m-nitrophenol, p-nitrophenol, o-nitroanisole, m-nitroanisole, p-nitroanisole, α-nitronaphthalene, β-nitronaphthalene, 2'-nitroacetophenone, 3'-nitroacetophenone, 3-nitrobenzophenone, 4-nitrobenzophenone, 4-nitroimidazole, o-nitrobenzonitrile, m-nitrobenzonitrile, p-nitrobenzonitrile, o-nitrobenzenesulfonic acid, m-nitrobenzenesulfonic acid, p-nitrobenzenesulfonic acid, o-nitrobenzenesulfonamide, m-nitrobenzenesulfonamide, p-nitrobenzenesulfonamide, o-(β-hydroxyethylsulfonyl)-nitrobenzene, m-(β-hydroxyethylsulfonyl)nitrobenzene and p-(β-hydroxyethylsulfonyl)nitrobenzene.

Catalysts

The homogeneous catalyst for preparing the aminoanthraquinones or aromatic amine compounds is prepared by dissolving at least a part of the rhodium compounds or ruthenium compounds is in solvents.

The rhodium compounds or ruthenium compounds are used for preparing aminoanthraquinones in the first aspect of the present invention. They are, preferably, complex compounds having carbonyl ligands, compounds which are able to form rhodium-carbonyl complexes or ruthenium-carbonyl complexes in the reaction system, or compounds which are able to form complexes with phosphine or phosphite. Compounds which are able to form carbonyl complexes under the reaction conditions are, for instance, carbonyl compounds, acetylacetonate salts, carboxylic acid salts, oxides, hydroxides, halides, nitrates, phosphates or ligand compounds. Compounds which are able to form complexes with phosphine or phosphite in a reaction system form the compounds of the formulas (III)–(V):

$$RhX(CO)_n(PR_3)_{3-n} \qquad (III)$$

$$RuH_mY_{2-m}(CO)_p(PR_3)_{4-p} \qquad (IV)$$

$$Ru(CO)_r(PR_3)_{5-r} \qquad (V)$$

wherein X is a hydrogen atom, a fluorine atom, a chlorine atom, a bromine atom or an iodine atom; Y is a fluorine atom, a chlorine atom, a bromine atom or an iodine atom; $PR_3$ is $PPh_3$, $PEtPh_2$, $PEt_2Ph$ or $P(OPh)_3$; n is zero or an integer up to 3; m is zero or an integer up to 2; p is zero or an integer up to 4; and r is zero or an integer up to 5.

Examples of the compounds of (III)–(V) are $Rh(CO)_2(acac)$, $[RhCl(COD)]_2$, $Rh_4(CO)_{12}$, $Rh_6(CO)_{16}$, $[Rh(CO)_2Cl]_2$, $Rh_2(OAc)_4$, $Rh(acac)_3$, $Rh_2O_3$, $RhO_2 \cdot 2H_2O$, $Rh_2O_3 \cdot 5H_2O$, $Rh(NO_3)_3$, $Rh_2(SO_4)_3$, $RhCl_3$, $RhBr_3$, $RhI_3$, $RhH(PPh_3)_3$, $PhF(PPh_3)_3$, $RhCl(PPh_3)_3$, $RhBr(PPh_3)_3$, $RhI(PPh_3)_3$, $RhH(CO)(PPh_3)_2$, $RhF(CO)(PPh_3)_2$, $RhCl(CO)(PPh_3)_2$, $RhBr(CO)(PPh_3)_2$, $RhI(CO)(PPh_3)_2$, $RhH(CO)_2(PPh_3)$, $RhF(CO)_2(PPh_3)$, $RhCl(CO)_2(PPh_3)$, $RhBr(CO)_2(PPh_3)$, $RhI(CO)_2(PPh_3)$, $RhH(PEtPh_2)_3$, $RhF(PEtPh_2)_3$, $RhCl(PEtPh_2)_3$, $RhBr(PEtPh_2)_3$, $RhI(PEtPh_2)_3$, $RhH(CO)(PEtPh_2)_2$, $RhF(CO)(PEtPh_2)_2$, $RhCl(CO)(PEtPh_2)_2$, $RhBr(CO)(PEtPh_2)_2$, $RhI(CO)(PEtPh_2)_2$, $RhH(CO)_2(PEtPh_2)$, $RhF(CO)_2(PEtPh_2)$, $RhCl(CO)_2(PEtPh_2)$, $RhBr(CO)_2(PEtPh_2)$, $RhI(CO)_2(PEtPh_2)$, $RhH(PEt_2Ph)_3$, $RhF(PEt_2Ph)_3$, $RhCl(PEt_2Ph)_3$, RhBr(PEt$_2$Ph)$_3$, RhI(PEt$_2$Ph)$_3$, RhH(CO)(PEt$_2$Ph)$_2$, RhF(CO)(PEt$_2$Ph)$_2$, RhCl(CO)(PEt$_2$Ph)$_2$, RhBr(CO)(PEt$_2$Ph)$_2$, RhI(CO)(PEt$_2$Ph)$_2$, RhH(CO)$_2$(PEt$_2$Ph), RhF(CO)$_2$(PEt$_2$Ph), RhCl(CO)$_2$(PEt$_2$Ph), RhBr(CO)$_2$(PEt$_2$Ph), RhI(CO)$_2$(PEt$_2$Ph), RhH(PEt$_3$)$_3$, RhF(PEt$_3$)$_3$, RhCl(PEt$_3$)$_3$, RhBr(PEt$_3$)$_3$, RhI(PEt$_3$)$_3$, RhH(CO)(PEt$_3$)$_2$, RhF(CO)(PEt$_3$)$_2$, RhCl(CO)(PEt$_3$)$_2$, RhBr(CO)(PEt$_3$)$_2$, RhI(CO)(PEt$_3$)$_2$, RhH(CO)$_2$(PEt$_3$), RhF(CO)$_2$(PEt$_3$), RhCl(CO)$_2$(PEt$_3$), RhBr(CO)$_2$(PEt$_3$), RhI(CO)$_2$(PEt$_3$), RhH(P(OPh)$_3$)$_3$, RhF(P(OPh)$_3$)$_3$, RhCl(P(OPh)$_3$)$_3$, RhBr(P(OPh)$_3$)$_3$, RhI(P(OPh)$_3$)$_3$, RhH(CO)(P(OPh)$_3$)$_2$, RhF(CO)(P(OPh)$_3$)$_2$, RhCl(CO)(P(OPh)$_3$)$_2$, RhBr(CO)(P(OPh)$_3$)$_2$, RhI(CO)(P(OPh)$_3$)$_2$, RhH(CO)$_2$(P(OPh)$_3$), RhF(CO)$_2$(P(OPh)$_3$), RhCl(CO)$_2$(P(OPh)$_3$), RhBr(CO)$_2$(P(OPh)$_3$), RhI(CO)$_2$(P(OPh)$_3$). Ru$_3$(CO)$_{12}$, H$_4$Ru$_4$(CO)$_{12}$, [RuCl$_2$(COD)]$_n$, [RuCl$_2$(CO)$_3$]$_2$, Ru(CO)$_5$, RuO$_2$, RuCl$_3$, RuBr$_3$, RuI$_3$, Ru(acac)$_3$, Ru(NO)(NO$_3$)$_3$, Ru(NO)Cl$_3$, H$_3$Ru(SO$_3$)$_2$OH, RuH$_2$(PPh$_3$)$_4$, RuH$_2$(CO)(PPh$_3$)$_3$, RuH$_2$(CO)$_2$(PPh$_3$)$_2$, RuH$_2$(CO)$_3$(PPh$_3$), RuH$_2$(CO)$_4$, RuHCl(PPh$_3$)$_4$, RuHCl(CO)(PPh$_3$)$_3$, RuHCl(CO)$_2$(PPh$_3$)$_2$, RuHCl(CO)$_3$(PPh$_3$), RuHCl(CO)$_4$, RuCl$_2$(PPh$_3$)$_4$, RuCl$_2$(CO)(PPh$_3$)$_3$, RuCl$_2$(CO)$_2$(PPh$_3$)$_2$, RuCl$_2$(CO)$_3$(PPh$_3$), RuCl$_2$(CO)$_4$, RuHBr(PPh$_3$)$_4$, RuHBr(CO)(PPh$_3$)$_3$, RuHBr(CO)$_2$(PPh$_3$)$_2$, RuHBr(CO)$_3$(PPh$_3$), RuHBr(CO)$_4$, RuBr$_2$(PPh$_3$)$_4$, RuBr$_2$(CO)(PPh$_3$)$_3$, RuBr$_2$(CO)$_2$(PPh$_3$)$_2$, RuBr$_2$(CO)$_3$(PPh$_3$), RuBr$_2$(CO)$_4$, RuHI(PPh$_3$)$_4$, RuHI(CO)(PPh$_3$)$_3$, RuHI(CO)$_2$(PPh$_3$)$_2$, RuHI(CO)$_3$(PPh$_3$), RuHI(CO)$_4$, RuI$_2$(PPh$_3$)$_4$, RuI$_2$(CO)(PPh$_3$)$_3$, RuI$_2$(CO)$_2$(PPh$_3$)$_2$, RuI$_2$(CO)$_3$(PPh$_3$), RuI$_2$(CO)$_4$, RuH$_2$(PEtPh$_2$)$_4$, RuH$_2$(CO)(PEtPh$_2$)$_3$, RuH$_2$(CO)$_2$(PEtPh$_2$)$_2$, RuH$_2$(CO)$_3$(PEtPh$_2$), RuHCl(PEtPh$_2$)$_4$, RuHCl(CO)(PEtPh$_2$)$_3$, RuHCl(CO)$_2$(PEtPh$_2$)$_2$, RuHCl(CO)$_3$(PEtPh$_2$), RuCl$_2$(PEtPh$_2$)$_4$, RuCl$_2$(CO)(PEtPh$_2$)$_3$, RuCl$_2$(CO)$_2$(PEtPh$_2$)$_2$, RuCl$_2$(CO)$_3$(PEtPh$_2$), RuHBr(PEtPh$_2$)$_4$, RuHBr(CO)(PEtPh$_2$)$_3$, RuHBr(CO)$_2$(PEtPh$_2$)$_2$, RuHBr(CO)$_3$(PEtPh$_2$), RuBr$_2$(PEtPh$_2$)$_4$, RuBr$_2$(CO)(PEtPh$_2$)$_3$, RuBr$_2$(CO)$_2$(PEtPh$_2$)$_2$, RuBr$_2$(CO)$_3$(PEtPh$_2$), RuHI(PEtPh$_2$)$_4$, RuHI(CO)(PEtPh$_2$)$_3$, RuHI(CO)$_2$(PEtPh$_2$)$_2$, RuHI(CO)$_3$(PEtPh$_2$), RuI$_2$(PEtPh$_2$)$_4$, RuI$_2$(CO)(PEtPh$_2$)$_3$, RuI$_2$(CO)$_2$(PEtPh$_2$)$_2$, RuI$_2$(CO)$_3$(PEtPh$_2$), RuH$_2$(P(OPh)$_3$)$_4$, RuH$_2$(CO)(P(OPh)$_3$)$_3$, RuH$_2$(CO)$_2$(P(OPh)$_3$)$_2$, RuH$_2$(CO)$_3$(P(OPh)$_3$), RuHCl(P(OPh)$_3$)$_4$, RuHCl(CO)(P(OPh)$_3$)$_3$, RuHCl(CO)$_2$(P(OPh)$_3$)$_2$, RuHCl(CO)$_3$(P(OPh)$_3$), RuCl$_2$(P(OPh)$_3$)$_4$, RuCl$_2$(CO)(P(OPh)$_3$)$_3$, RuCl$_2$(CO)$_2$(P(OPh)$_3$)$_2$, RuCl$_2$(CO)$_3$(P(OPh)$_3$), RuHBr(P(OPh)$_3$)$_4$, RuHBr(CO)(P(OPh)$_3$)$_3$, RuHBr(CO)$_2$(P(OPh)$_3$)$_2$, RuHBr(CO)$_3$(P(OPh)$_3$), RuBr$_2$(P(OPh)$_3$)$_4$, RuBr$_2$(CO)(P(OPh)$_3$)$_3$, RuBr$_2$(CO)$_2$(P(OPh)$_3$)$_2$, RuBr$_2$(CO)$_3$(P(OPh)$_3$), RuHI(P(OPh)$_3$)$_4$, RuHI(CO)(P(OPh)$_3$)$_3$, RuHI(CO)$_2$(P(OPh)$_3$)$_2$, RuHI(CO)$_3$(P(OPh)$_3$), RuI$_2$(P(OPh)$_3$)$_4$, RuI$_2$(CO)(P(OPh)$_3$)$_3$, RuI$_2$(CO)$_2$(P(OPh)$_3$)$_2$, RuI$_2$(CO)$_3$(P(OPh)$_3$), Ru(CO)$_4$(PPh$_3$). Ru(CO)$_3$(PPh$_3$)$_2$, Ru(CO)$_2$(PPh$_3$)$_3$, Ru(CO)(PPh$_3$)$_4$, Ru(PPh$_3$)$_5$, Ru(CO)$_4$(PEtPh$_2$), Ru(CO)$_3$(PEtPh$_2$)$_2$, Ru(CO)$_2$(PEtPh$_2$)$_3$, Ru(CO)(PEtPh$_2$)$_4$, Ru(PEtPh$_2$)$_5$, Ru(CO)$_4$(P(OPh)$_3$), Ru(CO)$_3$(P(OPh)$_3$)$_2$, Ru(CO)$_2$(P(OPh)$_3$)$_3$, Ru(CO)(P(OPh)$_3$)$_4$, Ru(P(OPh)$_3$)$_5$, etc.

Among them, the preferred are Rh$_4$(CO)$_{12}$, Rh$_6$(CO)$_{16}$, Ru$_3$(CO)$_{12}$, [RuCl$_2$(COD)]$_n$, [RuCl$_2$(CO)$_3$]$_2$, RuO$_2$, Ru(acac)$_3$, RuCl$_2$(CO)$_2$(PPh$_3$)$_2$, RuCl$_2$(CO)$_3$(PPh$_3$), RuCl$_2$(CO)$_3$(P(OPh)$_3$), Ru(CO)$_4$(PPh$_3$), etc.

The amount of the catalyst varies depending on reaction conditions but usually is $10^{-1}$—$10^{-5}$ mol per mol of the substrates for production of aminoanthraquinone.

The catalyst used for preparing the aromatic amines in the other aspect of the present invention are made up of ruthenium compounds. Preference are complexes having a carbonyl ligand, compounds which are able to form ruthenium-carbonyl complex and compounds which are able to form complexes with phosphine or phosphite. More specifically, the ruthenium compounds which are referred to in the production of the aminoanthraquinones in the first aspect of the present invention are used. Ru$_3$(CO)$_{12}$ is preferred. The amount of the catalyst used is usually $10^{-1}$—$10^{-5}$ mol, sometimes less than that, per mol of the substrate, although it may vary depending on reaction conditions.

Solvents

The presence of solvents is essential in the present processes. Some examples of the solvents for preparing the present aminoanthraquinones or aromatic amines are alcohols such as methanol, ethanol, isopropyl alcohol, n-propyl alcohol, n-butyl alcohol, isobutyl alcohol, n-pentyl alcohol, isoamyl alcohol and tertamyl alcohol; glymes such as diethylene glycol dimethyl ether, triethylene glycol dimethyl ether, tetraethylene glycol dimethyl ether, 2-methoxyethanol, 2-ethoxyethanol, 2-butoxyethanol, ethylene glycol, diethylene glycol, ethylene glycol dimethyl ether, ethylene glycol diethyl ether and ethylene glycol monoethyl ether acetate; ethers such as tetrahydrofuran, 1,4-dioxane and anisole; and ketons such as acetone, methylethylketone and methylisobutylketone.

Preferred for preparing the aminoanthraquinones in the first aspect of the present invention are methanol, ethanol, isopropyl alcohol, n-butyl alcohol, diethylene glycol dimethyl ether, triethylene glycol dimethyl ether and ethylene glycol monoethyl ether acetate. Preferred for preparing the aromatic amines in the other aspect of the present invention are methanol, ethanol, isopropyl alcohol, n-butyl alcohol, diethylene glycol dimethyl ether, triethylene glycol dimethyl ether and acetone. More preferable are methanol, ethanol, diethylene glycol dimethyl ether and acetone.

Amine compounds and copper compounds

As far as preparing aminoanthraquinones in the first aspect of the present invention is concerned, the homogeneous catalyst comprising the rhodium compounds or ruthenium compound and the solvents in the presence or absence of amine compounds, facilitates catalytic activity for preparing the aminoanthraquinones. Co-presence of the amine compounds mentioned above with the same catalyst as above greatly improves the catalytic activity. Furthermore, the use of the copper compounds mentioned below in addition to the amine compounds above in the case of homogeneous catalyst comprising the ruthenium compounds and the solvents additionally improves catalytic activity.

The amine compounds used in the first aspect of the present process, i.e., for preparing the present aminoanthraquinones are at least one amine compound selected from amines having the formula (I)

NR$^1$R$^2$R$^3$    (I), pyridines, imidazoles and chelate diamines. In the amines of the formula (I), R$^1$, R$^2$ and R$^3$ are each a hydrogen atom, an alkyl group or an aryl group but all of $R^1$, $R^2$ and $R^3$ are not hydrogen atoms. When one of $R^1$, $R^2$ and $R^3$ is a hydrogen atom and $R^1$, $R^2$ and $R^3$ all together form a ring, mention may be made of, for example, —(CH)$_4$—, —(CH$_2$)$_4$—, —(CH$_2$)$_5$— or —(CH$_2$)$_2$—NH—(CH$_2$)$_2$—. The pyridines are compounds having a pyridine skeleton and the imidazoles are compounds having an imidazole skeleton. The chelate diamines are chelate amines having two nitrogen atoms at 2,2'-, 1,2-, 2,3-, 9,10-, 1,3-, 1,4-, 1,5-, 1,8- or 1,10-positions.

Examples of the amine compounds used for preparing the present aminoanthraquinones in the first aspect of the invention are amines having C$_{1-5}$ alkyl groups such as trimethylamine, triethylamine, triisopropylamine, tri-n-propylamine, tri-n-butylamine, dimethylamine, diethylamine, diisopropylamine, di-n-butylamine, ethylamine, isopropylamine, n-propylamine, n-butylamine or ethyldiisopropylamine; amines having aryl groups such as aniline, 1-aminoanthraquinone, 2-aminoanthraquinone, N-methylaniline or N-ethylaniline; cyclic amines such as pyrrole, pyrrolidine, piperidine or piperazine; pyridines such as pyridine, α-picoline, β-picoline, γ-picoline, 4,4-dimethylaminopyridine, 2-cyanopyridine, 3-cyanopyridine, 4-cyanopyridine, 2-hydroxypyridine, 3-hydroxypyridine or 4-hydroxypyridine; imidazoles such as imidazole, N-methylimidazole, N-ethylimidazole, benzimidazole, 2-methylbenzimidazole or N-methylbenzimidazole; chelate diamines such as 9,10-diaminophenanthrene, 1,10-phenanthroline, 3,4,7,8-tetramethyl-1,10-phenanthroline, 3,4,5,6,7,8-hexamethyl-1,10-phenanthroline, o-phenylenediamine, N,N,N'N'-tetramethyl-o-phenylenediamine, 2,3-naphthalenediamine, 1,8-naphthalenediamine, 1,5-naphthalenediamine, 1,8-bis(dimethylamino)naphthalene or 2,3-bis(dimethylamino) naphthalene. Preferred amine compounds are triethylamine, tri-n-propylamine, diethylamine, diisopropylamine, 1-aminoanthraquinone, piperidine, 4-cyanopyridine, 2-methylbenzimidazole, 1,8-bis(dimethylamino) naphthalene and N,N,N',N'-tetramethyl-o-phenylenediamine.

The amine compounds are usually used in a mol amount of 0.01 to 500, preferably 0.01 to 300 times, as much as metal atoms in the catalyst.

Amines used in the other aspect of the present process, i.e., for preparing the present aromatic amines are those having the formula (II)

NHR$^4$R$^5$ (II)

wherein $R^4$ and $R^5$ are each a hydrogen atom, an alkyl group which may have substituents, a cycloalkyl group which may have substituents, an aralkyl group, an aryl group which may have substituents, but both $R^4$ and $R^5$ are not hydrogen atoms. The substituents are an alkyl group, a halogen atom, a hydroxyl group or an alkoxy group. When $R^4$ and $R^5$ together form a ring, mention is made of —(CH)$_4$—, —(CH$_2$)$_4$—, —(CH$_2$)$_5$— or —(CH$_2$)$_2$—NH—(CH$_2$)$_2$—.

Examples of the amines of the formula (II) are C$_1$–C$_8$ alkyl amines which may have substituents, such as methylamine, ethylamine, n-propylamine, isopropylamine, n-butylamine, iso-butylamine, tert.-butylamine, n-pentylamine, n-hexylamine, n-heptylamine, n-octylamine, dimethylamine, diethylamine, di-n-propylamine, di-isopropylamine, di-n-butylamine, di-isobutylamine, di-n-pentylamine, di-n-hexylamine, di-n-heptylamine, di-n-octylamine, ethylisopropylamine, 3-dimethylaminopropanol, 2-aminopropanol, 2-ethylhexylamine, 3-methoxypropylamine, 3-ethoxypropylamine, 2-chloroethylamine, bis(2-chloroethyl)amine or 3-chloroethylamine; C$_5$–C$_6$ cycloalkyl amines which may have substituents, such as cyclohexylamine, cyclopentylamine, dicyclohexylamine or 2,3-dimethylcyclohexylamine; aralkylamines such as benzylamine, dibenzylamine, N-benzylmethylamine or N-benzylethanolamine; arylamines which may have substituents, such as aniline, diphenylamine, o-toluidine, m-toluidine, p-toluidine, o-chloroaniline, m-chloroaniline, p-chloroaniline, o-anisidine, m-anisidine, p-anisidine, o-aminophenol, m-aminophenol or p-aminophenol; cyclic amines such as pyrrol, pyrrolidine, piperidine or piperazine. Preferred for preparing the aromatic amine compounds are diethylamine, diisopropylamine, di-n-butylamine, n-butylamine, pyrrolidine, piperidine, piperazine, dicyclohexylamine, benzylamine and o-chloroaniline.

The amines of the formula (II) are usually employed in a mol amount of 0.01 to 500, preferably, 0.01 to 100 times as much as the atoms in the catalyst.

Copper compounds used in the first aspect of the present process for producing aminoanthraquinones are copper compounds having a valence of one or two, i.e., oxides, halides, hydroxides, carboxylates, sulphates, nitrates and carbonates. For instance, they are cuprous oxide, cupric oxide, cuprous chloride, cupric chloride, cuprous bromide, cupric bromide, cuprous iodide, cupric iodide, copper hydroxide, copper acetate, copper oxalate, copper formate, copper naphthenate, copper stearate, copper sulphate, copper nitrate and copper carbonate. Preferred are cupric oxide, copper carbonate, cupric bromide and copper acetate.

The copper compounds are usually employed in a mol amount of 0.01–500 times, preferably 0.01–100 times as much as the metal atoms in the catalyst.

Reaction conditions

Reaction temperature is usually 0° to 250° C., preferably 20° to 200° C.

CO pressure is not critical but usually 1 to 100 atm., although higher pressure may be employed.

One of the aspect of the present process for preparing aminoanthra quinones proceeds under CO/H$_2$O in a liquid phase, keeping catalytic activity at high level. Reduction of only the nitro group is effected with high selectivity, resulting in obtaining the desired aminoanthraquinones, in high yield. The aminoanthraquinones are readily separated by filtration from the catalysts which are recycled with ease, since the aminoanthraquinones are hardly dissolved and precipitated in the crystal form.

Another aspect of the present process for preparing aromatic amine compounds achieves production of the corresponding aromatic amine compounds with high selectivity and high yield, since only nitro groups are selectively reduced while catalyst activity is not substantially damaged. Reduction of the nitro group proceeds with priority, while such side-reactions as water-gas-shift reaction are controlled.

Examples

Example 1

In an autoclave (10 cc) made of stainless steel and equipped with a stirrer drivable by magnetic force, there were charged Ru$_3$(CO)$_{12}$ (0.005 mmol), methanol (15 ml), water (5 ml) and 1-nitroanthraquinone (3.0 g, 10.2 mmol, produced by Tokyo Kasei, Japan, purity:

86.2%, anthraquinone: 13.8%). The contents were stirred under CO (20 Kg/cm$^2$) at 150° C. for 2 hours.

Reaction product was assayed by gas chromatography and liquid chromatography. Identification was made by comparison of retention time of chromatogram, elemental assay and GC-MS.

Index of catalytic activity was based on total turn-over number (TN).

Total turn-over number (TN)=amount of aminoanthraquinones or aromatic amine compounds produced (mmol)/amount of catalyst (mmol)

The assay of the reaction product showed that there was only 1-aminoanthraquinone (4.8 mmol) and no by-product. Selectivity of nitro group=100%, TN=969.

The same assay procedure was repeated in the following examples and comparison examples.

Examples 2–40

Example 1 was repeated except that the solvents mentioned in Table 1 were used in place of the methanol and the amine compounds mentioned in Table 1 were added.

Assay of the reaction products showed that there were only 1-aminoanthraquinones and no by-products. Selectivity of nitro group each: 100%.

The results are shown in Table 1.

TABLE 1

| Example Nos. | Amine compounds | Mol ratios[1] | Solvents | 1-Aminoanthraquinones produced (mmol) | TN |
|---|---|---|---|---|---|
| 2 | 3,4,7,8-Tetramethyl-1,10-phenanthroline | 0.5 | Methanol | 4.96 | 992 |
| 3 | N,N,N',N'-Tetramethyl-o-phenylenediamine | 1.5 | Methanol | 5.12 | 1024 |
| 4 | N,N,N',N'-Tetramethyl-o-phenylenediamine | 1.5 | Diethylene glycol Dimethyl ether | 6.92 | 1384 |
| 5 | 1,8-Bis(dimethylamino)naphthalene | 3 | Methanol | 5.20 | 1040 |
| 6 | 1,8-Bis(dimethylamino)naphthalene | 10 | Methanol | 6.02 | 1204 |
| 7 | 1,8-Bis(dimethylamino)naphthalene | 20 | Methanol | 7.69 | 1538 |
| 8 | 1,8-Bis(dimethylamino)naphthalene | 50 | Methanol | 5.70 | 1140 |
| 9 | 4-Cyanopyridine | 3 | Diethylene glycol Dimethyl ether | 6.12 | 1242 |
| 10 | 4-Cyanopyridine | 6 | Diethylene glycol Dimethyl ether | 5.56 | 1112 |
| 11 | γ-Picoline | 3 | Diethylene glycol Dimethyl ether | 5.42 | 1084 |
| 12 | 2-Methylbenzimidazole | 1 | Diethylene glycol Dimethyl ether | 5.68 | 1136 |
| 13 | Pyrrole | 10 | Methanol | 5.46 | 1092 |
| 14 | Pyrrolidine | 3 | Methanol | 5.36 | 1072 |
| 15 | Pyrrolidine | 6 | Methanol | 6.11 | 1222 |
| 16 | Pyrrolidine | 20 | Methanol | 5.14 | 1028 |
| 17 | Piperidine | 1 | Methanol | 5.99 | 1198 |
| 18 | Piperidine | 3 | Methanol | 7.80 | 1560 |
| 19 | Piperidine | 20 | Methanol | 5.71 | 1142 |
| 20 | Piperidine | 1 | Diethylene glycol Dimethyl ether | 5.97 | 1194 |
| 21 | Piperidine | 3 | Isopropyl alcohol | 5.39 | 1078 |
| 22 | Piperidine | 1 | Triethylene glycol Dimethyl ether | 5.66 | 1132 |
| 23 | Piperidine | 3 | Triethylene glycol Dimethyl ether | 5.31 | 1062 |
| 24 | Piperidine | 3 | Ethanol | 5.97 | 1194 |
| 25 | Piperazine | 3 | Methanol | 5.45 | 1091 |
| 26 | Piperazine | 6 | Methanol | 5.41 | 1082 |
| 27 | Triethylamine | 50 | Methanol | 5.71 | 1141 |
| 28 | Triethylamine | 100 | Methanol | 7.26 | 1453 |
| 29 | Triethylamine | 200 | Methanol | 6.58 | 1316 |
| 30 | Triethylamine | 100 | Ethanol | 6.81 | 1362 |
| 31 | Tri-n-propylamine | 3 | Methanol | 6.05 | 1210 |
| 32 | Tri-n-propylamine | 10 | Methanol | 6.26 | 1252 |
| 33 | Tri-n-propylamine | 3 | Diethylene glycol Dimethyl ether | 5.10 | 1020 |
| 34 | Diethylamine | 100 | Methanol | 6.77 | 1354 |
| 35 | Diethylamine | 200 | Methanol | 6.87 | 1374 |
| 36 | Diethylamine | 100 | Diethylene glycol | 5.33 | 1065 |

TABLE 1-continued

| Example Nos. | Amine compounds | Mol ratios[1] | Solvents | 1-Amino-anthraquinones produced (mmol) | TN |
| --- | --- | --- | --- | --- | --- |
| 37 | Diisopropylamine | 10 | Dimethyl ether Methanol | 6.70 | 1340 |
| 38 | Diisopropylamine | 20 | Methanol | 7.08 | 1416 |
| 39 | Diisopropylamine | 50 | Methanol | 5.36 | 1072 |
| 40 | 1-Aminoanthraquinone | 20 | Diethylene glycol Dimethyl ether | 5.12 | 994 |

[1] Mol ratios = Amine compounds (mmol)/metal atoms in catalysts (mmol)

Examples 41–43

Example 1 was repeated except that $Rh_6(CO)_{16}$ (0.005 mmol) and the solvents mentioned in Table 2 were used in place of the $Ru_3(CO)_{12}$ (0.005 mmol) and the methanol, respectively.

Assay of the reaction products showed that there were only 1-aminoanthraquinones and no by-products. Selectivity of nitro group each: 100%.

The results are shown in Table 2.

TABLE 2

| Example Nos. | Solvents | 1-Amino-anthraquinones produced (mmol) | TN |
| --- | --- | --- | --- |
| 41 | Methanol | 6.12 | 1224 |
| 42 | Ethylene glycol Monoethyl ether | 5.79 | 1158 |
| 43 | Ethanol | 5.10 | 1020 |

Examples 44–48

Example 42 was repeated except that amine compounds shown in Table 3 were added.

Assay of the reaction products showed that there were only 1-aminoanthraquinones and no by-products. Selectivity of nitro group each = 100%.

The results are shown in Table 3.

TABLE 3

| Example Nos. | Amine compounds | Mol ratios[1] | 1-Amino-anthraquinones produced (mmol) | TN |
| --- | --- | --- | --- | --- |
| 44 | Triethylamine | 50 | 7.53 | 1506 |
| 45 | Tri-n-propylamine | 10 | 7.50 | 1500 |
| 46 | 9,10-Diamino-phenanthrene | 10 | 7.11 | 1422 |
| 47 | Imidazole | 1 | 6.78 | 1356 |
| 48 | Diisopropylamine | 50 | 9.12 | 1824 |

Note:
Mol ratios = amine compounds (mmol)/metal atoms in catalyst (mmol)

Example 49

Example 1 was repeated except that $Rh_4(CO)_{12}$ (0.005 mmol), 3,4,7,8-tetramethyl-1,10-phenanthroline (0.005 mmol) and ethanol were used in place of the $Ru_3(CO)_{12}$ (0.005 mmol), 1-nitroanthraquinone and methanol, respectively.

Assay of the reaction product showed that there was only 1-aminoanthraquinone (1.72 mmol) and no by-product. Selectivity of nitro group = 100%, TN = 345.

Example 50

Example 49 was repeated except that 4,4-dimethylaminopyridine (1.5 mmol) and 2-methoxyethanol were used in place of the 3,4,7,8-tetramethyl-1,10-phenanthroline (0.005 mmol) and ethanol.

Assay of the reaction product showed that there was only 1-aminoanthraquinone (1.68 mmol) and no by-product. Selectivity of nitro group = 100%, TN = 337.

Examples 51–55

Example 1 was repeated except that triethylamine (1.5 mmol) was added to each and the reactions were carried out under reaction temperatures and CO pressures as shown in Table 4 in place of 150° C. and 20 Kg/cm$^2$, respectively. In Examples 53–55, reactions were effected for 90 min. in place of the 2 hours.

Assay of the reaction products showed that there were only 1-aminoanthraquinones and no by-products. Selectivity of nitro group each: 100%.

The results are shown in Table 4.

TABLE 4

| Example Nos. | Reaction temperatures (°C.) | CO pressures (Kg/cm$^2$) | 1-Amino-anthraquinones produced (mmol) | TN |
| --- | --- | --- | --- | --- |
| 51 | 120 | 20 | 3.11 | 622 |
| 52 | 180 | 20 | 9.85 | 1971 |
| 53 | 150 | 10 | 3.22 | 643 |
| 54 | 150 | 20 | 4.26 | 852 |
| 55 | 150 | 30 | 5.81 | 1162 |

Examples 56 and 57

Example 1 was repeated except that 0.002 mmol each of $Ru_3(CO)_{12}$ was used in place of the 0.005 mmol, triethylamine (1.5 mmol) was added to each 180° C. was used in place of the 150° C. and the solvents shown in Table 5 were used in place of the methanol.

Assay of the reaction products showed that there were only 1-aminoanthraquinones and no by-products. Selectivity of nitro group each = 100%.

The results are shown in Table 5.

TABLE 5

| Example Nos. | Solvents | 1-Amino-anthraquinones produced (mmol) | TN |
| --- | --- | --- | --- |
| 56 | Methanol | 5.41 | 2705 |
| 57 | Diethylene glycol Dimethyl ether | 4.70 | 2348 |

Example 58

Example 1 was repeated except that $Ru_3(CO)_{12}$ (0.01 mmol) was used in place of the (0.005 mmol), triethylamine (1.5 mmol) was added and ethanol was used in place of the methanol.

Assay of the reaction product showed that there was only 1-aminoanthraquinone and no by-product. Selectivity of nitro group = 100%, TN = 1020.

Example 59

Example 28 was repeated except that 5 hours for reaction period of time was used in place of the 2 hours.

Assay of the reaction product showed that there was only 1-aminoanthraquinone and no by-product. Selectivity of nitro group=100%, TN=2040.

Assay of gas obtained after the reaction was over gave

| $CO_2$ | 30.2 mmol |
|---|---|
| $H_2$ | 0.02 mmol. |

An amount of $H_2$ was very small.

Example 60

Example 14 was repeated except 5 hours for reaction period of time, $Ru_3(CO)_{12}$ (0.0 and pyrrolidine (0.045 mmol) were used in place of 2 hours, 0.005 mmol and 0.015 mmol (=0.005 mmol×3), respectively.

Assay of the reaction product showed that there was only 1-aminoanthraquinone (10.2 mmol) and no by-product. Selectivity of nitro group=100%, TN=1020.

Assay of gas obtained after the reaction was over gave

| $CO_2$ | 34.2 mmol |
|---|---|
| $H_2$ | 0.08 mmol. |

An amount of $H_2$ was very small.

Example 61

In an autoclave (110 cc) made of stainless steel and equipped with a stirrer drivable by magnetic force there were charged $Ru_3(CO)_{12}$ (0 01 mmol), methanol (15 ml), water (5 ml), triethylamine (1.5 mmol) and nitroanthraquinone (2 g). Stirring was made under CO (20 Kg/cm²) at 150° C. for 6 hours. The nitroanthraquinone contained mononitroanthraquinone (74.9%), dinitroanthraquinone (23.5%) and anthraquinone (1.6%).

Assay of the reaction product showed that there were no nitro groups left unchanged but only the corresponding 1-aminoanthraquinone, 2-aminoanthraquinone, 1,5-diaminoanthraquinone and 1,8-diaminoanthraquinone. Selectivity of nitro group=100%. Yield of aminoanthraquinones=99% or more.

Example 62

Example 61 was repeated except that isopropyl alcohol was used in place of the methanol.

Assay of the reaction product showed that there were no nitro groups left unchanged in the reaction product but only the corresponding aminoanthraquinones. Selectivity of nitro group=100%. Yield of aminoanthraquinones=99% or more.

Example 63

Example 61 was repeated except that diethylene glycol dimethyl ether and piperidine (0.09 mmol) were used in place of the methanol and triethylamine (1.5 mmol).

Assay of the reaction product showed that 98% of the 1-nitroanthraquinone was reduced to produce 1-aminoanthraquinone and the nitro groups of all the other nitroanthraquinones were reduced to produce the corresponding aminoanthraquinones. Selectivity of nitro group=100%. Yield of aminoanthraquinones=98% or more.

Example 64

In an autoclave (260 ml) equipped with a thermometer, a stirrer with turbine blades, cooling pipes and a CO gas feeder at the bottom, there were charged $Ru(acac)_3$, (0.10 mmol), ethylene glycol monoethyl ether acetate (60 ml), water (23 ml), aminoanthraquinone (0.11 g) and nitroanthraquinone (10 g). Stirring (800 rpm) was made under CO (20 Kg/cm², 500 ml/min.) at 170° C. for 3 hours. The nitroanthraquinone feed contained 74.9% of mononitroanthraquinone, 23.5% of dinitroanthraquinone and 1.6% of anthraquinone. The aminoanthraquinone feed contained 74.9% of monoaminoanthraanthraquinone quinone, 23.5% of diaminoanthraquinone and 1.6% of anthraquinone.

Assay of the reaction product showed that there were no nitro group left unchanged but only the corresponding 1-aminoanthraquinone, 2-aminoanthraquinone, 1,5-diaminoanthraquinone and 1,8-diaminoanthraquinone. Selectivity of nitro group=100%. Yield of aminoanthraquinones=99.9% or more.

Example 65

Example 64 was repeated except that $Ru_3(CO)_{12}$ 0.04 mmol). n-butyl alcohol, the same aminoanthraquinone (88 mg) and 2 hours of reaction period of time were used in place of the $Ru(acac)_3$, ethylene glycol monoethyl ether acetate, 0.11 g and 3 hours, respectively.

Assay of the reaction product showed that there were no nitro group left unchanged but only the corresponding 1-aminoanthraquinone, 2-aminoanthraquinone, 1,5-diaminoanthraquinone and 1,8-diaminoanthraquinone. Selectivity of nitro group=100%. Yield of aminoanthraquinones=86%.

Example 66

Example 65 was repeated except that ethylene glycol monoethyl ether acetate was used in place of the n-butyl alcohol.

Assay of the reaction product showed that there were no nitro group left unchanged but only the corresponding 1-aminoanthraquinone, 2-aminoanthraquinone, 1,5-diaminoanthraquinone and 1,8-diaminoanthraquinone. Selectivity of nitro group=100%. Yield of aminoanthraquinones=90%.

Examples 67-70

Example 66 was repeated except that $[RuCl_2(COD)]_n$ (0.1 mmol, produced by Kanto Kagaku, Japan) or $RuO_2$ (0.1 mmol) to which the additives shown in Table 6 are present was used in place of the $Ru_3(CO)_{12}$ the reaction proceeded for 3 hours instead of 2 hours.

Assay of the reaction products showed that there were no nitro group left unchanged and only the corresponding 1-aminoanthraquinones, 2-aminoanthraquinones, 1,5-diaminoanthraquinone and 1,8-diaminoanthraquinone anthraquinones were present. Selectivity of nitro group=100%.

The results are shown in Table 6 wherein TNs per nitro group were used as indexes for catalytic activities.

TABLE 6

| Example Nos. | Catalysts | Additives (mmol) | TN |
|---|---|---|---|
| 67 | $[RuCl_2(COD)]_n$ | Triphenylphosphine 0.32 | 412 |
| 68 | $[RuCl_2(COD)]_n$ | Triphenylphosphite 0.10 | 375 |
| 69 | $[RuCl_2(COD)]_n$ | — | 264 |
| 70 | $RuO_2$ | Triphenylphosphine 0.08 | 402 |

Examples 71–74

In an autoclave (110 ml) made of stainless steel and equipped with a stirrer drivable with magnetic force there were charged $Ru(CO)_{12}$ (0.005 mmol), ethylene glycol monoethyl ether acetate (15 ml), water (5 ml), triethylamine (1.5 mmol), nitroanthraquinone (2 g) and one of the copper compounds shown in Table 7. Stirring was effected under CO (20 Kg/cm$^2$) at 150° C. for 2 hours. The nitroanthraquinone above was the same as in that in Example 64.

Assay of the reaction products showed that there were only aminoanthraquinones and no by-products. Selectivity of nitro group=100%. Total turn-over numbers per nitro group were used as indexes of catalyst activities.

The results are shown in Table 7.

TABLE 7

| Example Nos. | Copper compounds | Mol ratios[1] | TN |
|---|---|---|---|
| 71 | Cupric oxide | 20 | 1679 |
| 72 | Copper carbonate | 16 | 1532 |
| 73 | Cupric bromide | 30 | 1203 |
| 74 | Copper acetate | 25 | 1193 |

[1] Copper atom (mmol)/metal atom in catalyst (mmol)

Example 75

Example 72 was repeated except that $Ru_3(CO)_{12}$ (0.003 mmol), nitroanthraquinone (3 g), temperature of 180° C. and CO (50 Kg/cm$^2$) were used in place of the $Ru(CO)_{12}$ (0.005 mmol), nitroanthraquinone (2 g), 150° C. and 20 Kg/cm$^2$, respectively.

Assay of the reaction product showed that there were no nitro group left unchanged but only the corresponding 1-aminoanthraquinone, 2-aminoanthraquinone, 1,5-diaminoanthraquinone and 1,8-diaminoanthraquinone, were present without any by-product. Selectivity of nitro group=100%. TN=4932.

Examples 76–80

In an autoclave (50 cc) made of stainless steel and equipped with a stirrer drivable by magnetic force there were charged $Ru_3(CO)_{12}$(0.003 mmol), ethanol (5 ml), water (2 ml), one of amines shown in Table 8 and nitrobenzene (about 5 mmol). Stirring was made under CO (20 Kg/cm$^2$) at 150° C. for 100 min.

Assay of the reaction products showed that there were anilines without any by-products.

The results are shown in Table 8.

Comparison Example 1

Example 76 was repeated except that 3,4,7,8-tetramethyl-1,10-phenanthroline (0.0045 mmol) was used in place of the diisopropylamine.

Assay of the reaction product showed that there was only aniline without any by-product.

The result is shown in Table 8.

TABLE 8

| Nos. | Amines | Mol ratios[1] | TN |
|---|---|---|---|
| Example 76 | Diisopropylamine | 50 | 1587 |
| Example 77 | n-Butylamine | 20 | 1722 |
| Example 78 | Piperazine | 5 | 1568 |
| Example 79 | Benzylamine | 5 | 1581 |
| Example 80 | o-Chloroaniline | 5 | 1322 |
| Comparison Example 1 | 3,4,7,8-Tetramethyl-1,10-phenanthroline | 0.5 | 1080 |

Examples 81–87

Example 76 was repeated except that ethanol (10 ml), water (4 ml), nitrobenzene (about 10 mmol) and amines shown in Table 9 were used in place of the ethanol (5 ml), water (2 ml), nitrobenzene (about 5 mmol) and diisopropylamine, respectively.

Assay of the reaction products showed that there were anilines without by-products.

The results are shown in Table 9.

TABLE 9

| Example Nos. | Amines | Mol ratios[1] | TN |
|---|---|---|---|
| 81 | Pyrrolidine | 5 | 1573 |
| 82 | Piperidine | 3 | 1524 |
| 83 | Diisopropylamine | 50 | 1683 |
| 84 | Diisopropylamine | 70 | 2016 |
| 85 | Diethylamine | 25 | 1510 |
| 86 | Di-n-butylamine | 35 | 1833 |
| 87 | Dicyclohexylamine | 50 | 1694 |

[1] Mol ratio = amine (mmol)/metal atom in catalyst (mmol)

Examples 88–90

Example 81 was were repeated except that one of the amines shown in Table 10 and reaction temperature of 180° C. were used in place of the pyrrolidine and 150° C., respectively.

Assay of the reaction products showed that there were only anilines and no by-products.

The results are shown in Table 10.

TABLE 10

| Example Nos. | Amines | Mol ratios[1] | TN | Yields % |
|---|---|---|---|---|
| 88 | Piperidine | 3 | 3422 | >97 |
| 89 | Diisopropylamine | 50 | 3421 | >98 |
| 90 | Diethylamine | 25 | 3448 | >98 |

[1] Mol ratio = amine (mmol)/metal atom in catalyst (mmol)

Examples 91–94

Examples 84 was repeated except that the solvents shown in Table 11 was used in place of the ethanol.

Assay of the reaction products showed that there were only anilines and no by-products.

The results are shown in Table 11.

TABLE 11

| Example Nos. | Solvents | TN |
|---|---|---|
| 91 | Methanol | 1707 |
| 92 | Isoamyl alcohol | 1665 |
| 93 | Diethylene glycol dimethyl ether | 1944 |
| 94 | Acetone | 1919 |

Example 95

In an autoclave (110 cc) equipped with a stirrer there were charged $Ru_3(CO)_{12}$ (0.01 diisopropylamine (1.5 mmol), diethylene glycol dimethyl ether (15 ml), water (5 ml) and o-chloronitrobenzene (5 mmol). Stirring was effected under CO (20 Kg/cm$^2$) at 150° C. for 2 hours in order to allow a reaction to proceed.

After the reaction was over, assay of the reaction product showed that there was only o-chloroaniline and no by-product. Yield of o-chloroaniline=99% or more.

Assay of the gas after the reaction was over gave

| $H_2$ | 0.4 mmol |
|---|---|
| CO | 72.3 mmol |
| $CO_2$ | 14.7 mmol. |

Example 96

Example 95 was repeated except that an autoclave (50 cc) equipped with a stirrer drivable by magnetic force and o-bromonitrobenzene were used in place of the autoclave (110 cc) and o-chloronitrobenzene.

Assay of the reaction product showed that there was only o-bromoaniline (yield=99% or more) and no by-product.

Example 97

Example 96 was repeated except that p-chloronitrobenzene was used in place of the o-bromonitrobenzene.

Assay of the reaction product showed that there was only p-chloroaniline (yield=99% or more) and no by-products.

Example 98

Example 96 was repeated except that p-cyanonitrobenzene was used in place of the o-bromonitrobenzene.

Assay of the reaction product showed that there was only p-aminobenzonitrile (yield=99% or more) and no by products.

Example 99

Example 96 was repeated except that p-nitrobenzophenone was used in place of the o-bromonitrobenzene.

Assay of the reaction product showed that there was only p-aminobenzophenone (yield=99% or more) and no by-products.

Comparison Example 2

Example 96 was repeated except that acetophenone was used in place of the o-bromonitrobenzene.

Assay of the reaction product showed that there was only acetophenone with no other compounds.

Comparison Example 3

Example 96 was repeated except that phenylacetylene was used in place of the o-bromonitrobenzene.

Assay of the reaction product showed that there was only phenylacetylene with no other compounds.

Comparison Example 4

Example 95 was repeated except that benzonitrile was used in place of the o-chloronitrobenzene.

Assay of the reaction product showed that there were only benzonitrile with no other compounds. Assay of the gas after the reaction was over gave

| $H_2$ | 0.4 mmol |
|---|---|
| CO | 94.9 mmol |
| $CO_2$ | —. |

I claim:

1. A process for preparing aromatic amine compounds which comprises reacting aromatic nitro compounds excluding nitroanthraquinones with carbon monoxide and water in the presence of a homogeneous catalyst comprising ruthenium compounds and solvents therefor as well as amines having the formula (II)

$$HNR^4R^5 \qquad \text{II}$$

wherein $R^4$ and $R^5$ each is a hydrogen atom, an alkyl group, a cycloalkyl group, an aralkyl group or an aryl group but both $R^4$ and $R^5$ are not hydrogen atoms, and $R^4$ and $R^5$ may together form a ring and wherein said alkyl group, said cycloalkyl group and said aryl group may have substituents selected from the group consisting of an alkyl group, a halogen atom and an alkoxy group.

2. A process for preparing aromatic amine compounds according to claim 1 wherein the ruthenium compounds are complexes having carbonyl ligands, those which are capable of forming carbonyl complexes in the reaction system or those which are capable of forming complexes with phosphine or phosphite.

3. A process for preparing aromatic amine compounds according to claim 2 wherein the ruthenium compounds are $Ru_3(CO)_{12}$.

4. A process for preparing aromatic amine compounds according to claim 1 wherein the amines of the formula (II) are diethylamine, diisopropylamine, di-n-butylamine, n-butylamine, pyrrolidine, piperidine, piperazine, benzylamine, o-chloroaniline or dicyclohexylamine.

5. A process for preparing aromatic amine compounds according to claim 1 wherein the amines are used in a molar amount of 0.01-500 times the molar amount of metal atoms of the catalyst used.

6. A process for preparing aromatic amine compounds according to claim 5 wherein the amines are used in a molar amount of 0.01-100 times the molar amount of metal atoms of the catalyst used.

7. A process for preparing aromatic amine compounds according to claim 1 wherein the reaction is conducted at 0°-250° C.

8. A process for preparing aromatic amine compounds according to claim 1 wherein the carbon monoxide is under pressure of 1-100 atmospheres.

* * * * *